(12) United States Patent
Ohba et al.

(10) Patent No.: US 9,592,183 B2
(45) Date of Patent: Mar. 14, 2017

(54) INHIBITOR OF ENDOTHELIN ACTION AND SKIN-WHITENING AGENT

(75) Inventors: Tsuyoshi Ohba, Utsunomiya (JP); Daiki Murase, Mason, OH (US); Mitsuru Sugiyama, Utsunomiya (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/993,454

(22) PCT Filed: Nov. 24, 2011

(86) PCT No.: PCT/JP2011/077060
§ 371 (c)(1),
(2), (4) Date: Aug. 14, 2013

(87) PCT Pub. No.: WO2012/081370
PCT Pub. Date: Jun. 21, 2012

(65) Prior Publication Data
US 2013/0330286 A1    Dec. 12, 2013

(30) Foreign Application Priority Data

Dec. 13, 2010  (JP) ................. 2010-277001
Dec. 13, 2010  (JP) ................. 2010-277002

(51) Int. Cl.
| A61K 8/37 | (2006.01) |
| A61Q 19/02 | (2006.01) |
| A61K 31/235 | (2006.01) |
| A61K 8/99 | (2006.01) |
| A61K 36/09 | (2006.01) |

(52) U.S. Cl.
CPC ............... *A61K 8/37* (2013.01); *A61K 8/375* (2013.01); *A61K 8/99* (2013.01); *A61K 31/235* (2013.01); *A61K 36/09* (2013.01); *A61Q 19/02* (2013.01); *A61K 2800/782* (2013.01)

(58) Field of Classification Search
CPC ........ A61K 31/325; A61K 8/375; A61K 8/37; A61Q 19/00; A61Q 19/02; A61Q 19/08
See application file for complete search history.

(56) References Cited

U.S. PATENT DOCUMENTS 5,409,702 A * 4/1995 Higuchi ................. A61Q 19/02 424/195.15
2004/0146539 A1 * 7/2004 Gupta ........................... 424/401

FOREIGN PATENT DOCUMENTS

| JP | 1990-223517 A | 9/1990 |
| JP | 07-069882 A | 3/1995 |
| JP | 2005082531 A * | 3/2005 |
| JP | 2006-182731 A | 7/2006 |
| JP | 2007269743 A * | 10/2007 |
| JP | 2010-241715 A | 10/2010 |
| JP | 2012-006853 A | 1/2012 |
| JP | 2012-020950 A | 2/2012 |
| JP | 2013-032311 A | 2/2013 |
| KR | 10-2007-0015261 A | 2/2007 |

OTHER PUBLICATIONS

Raw Machine Translation of JP2005-82531 retrieved from Patent Abstracts of Japan on Jun. 30, 2014.*
Raw Machine Translation of JP2007-269743 retrieved from Patent Abstracts of Japan on Jun. 30, 2014.*
Bayir, Y.; Odabasoglu, F.; Cakir, A.; Aslan, A.; Suleyman, H.; Halici, M.; Kazaz, C. The inhibition of gastric mucosal lesion, oxidative stress and neutrophil-infiltration in rats by lichen constituent diffractaic acid. Phytomedicine, 2006, 13, p. 584-590.*
https://www.goldenlotusherbs.com/index.php?pageid=2&itemid=339 cited Nov. 5, 2015.*
International Search Report (ISR) for PCT/JP2011/077060; I.A. fd: Nov. 24, 2011, mailed Feb. 14, 2012 from the Japanese Patent Office, Tokyo, Japan.
International Preliminary Report on Patentability (IPRP), Chapter I of the Patent Cooperation Treaty, including the Written Opinion for PCT/JP2011/077060; I.A. fd: Nov. 24, 2011, issued Jun. 18, 2013, from the International Bureau of WIPO, Geneva, Switzerland.
Hirata, Y et al., "Cellular mechanism of action by a novel vasoconstrictor endothelin in cultured rat vascular smooth muscle cells," Biochem Biophys Res Commun 154(3): 868-875 (Aug. 1988), Academic Press, San Diego, CA.
Imokawa, G et al., "Endothelins secreted from keratinocytes are intrinsic mitogens for human melanocytes," J Biol Chem 267: 24675-24680 (Dec. 1992), Am Soc for Biochem Molec Biol, Bethesda, MD.
Imokawa, G et al., "Endothelin-1 as a new melanogen: coordinated expression of its gene and the tyrosinase gene in UVB-exposed human epidermis," J Invest Dermatol 105(1): 32-37, (Jul. 1995), Nature Publishing Group, New York.

(Continued)

*Primary Examiner* — Jessica Worsham
(74) *Attorney, Agent, or Firm* — Sterne, Kessler, Goldstein & Fox P.L.L.C.

(57) ABSTRACT

An inhibitor of endothelin action or a skin-whitening agent, comprising a compound represented by Formula (1) or a salt thereof as an active ingredient:

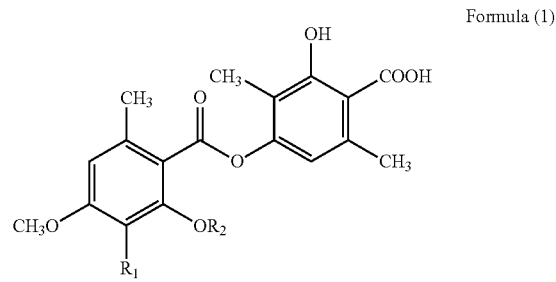

Formula (1)

wherein in Formula (1), $R_1$ represents a formyl group or an alkyl group having 1 to 4 carbon atom(s), and $R_2$ represents a hydrogen atom or an alkyl group having 1 to 4 carbon atom(s).

9 Claims, 2 Drawing Sheets

(56) References Cited

OTHER PUBLICATIONS

Kadono, S et al., "The role of the epidermal endothelin cascade in the hyperpigmentation mechanism of lentigo senilis," J Invest Dermatol 116(4): 571-577, (Apr. 2001), Nature Publishing Group, New York.

Kawahara, N et al., "About the component of snow tea," Collection of Pharmaceutical Society of Japan annual convention subject matter, p. 159, Abstract 30-0823, 125th Annual Meeting Pharmaceutical Society of Japan, Mar. 25-31, 2005, Tokyo, Japan.

Yada, Y et al., "Effects of endothelins on signal transduction and proliferation in human melanocytes," J Biol Chem, Sep. 1991; 266: 18352-18357 (Sep. 1991), Am Soc for Biochem Molec Biol, Bethesda, MD.

"Four outside," New Cosmetics Handbook, Nikkou Chemical Co., Ltd and others, Oct. 30, 2006, pp. 527-529, excerpted English translation.

"Ultraviolet damage preventive," New Cosmetics Handbook, Nikkou Chemical Co., Ltd and others, Oct. 30, 2006, Chapter 6, pp. 564-567, excerpted English translation.

Patentscope English language title and abstract for KR 10-2007-0015261 A, WIPO, Geneva Switzerland.

Aoki, H., "Recent Melanin Pigment Research," Fragrance Journal, Sep. 2008, No. 338, vol. 36(9), p. 14.

Kawahara, N. et al., "Studies on Chemical Components and HPLC Profile Analysis of Setsucha Products," Japanese Journal of Food Chemistry, 2007, 14(2):63-69.

\* cited by examiner

INHIBITOR OF ENDOTHELIN ACTION AND SKIN-WHITENING AGENT

TECHNICAL FIELD

The present invention relates to an inhibitor of endothelin action and a skin-whitening agent.

Further, the present invention relates to a method of producing a whiteworm lichen extract containing a high concentration of baeomycesic acid which is preferably used for an active ingredient of the inhibitor or skin-whitening agent.

BACKGROUND ART

Endothelin is an endothelial cell-derived peptide hormone capable of acting on various cells and tissues through its receptors. For example, endothelin is known to cause a rise in intracellular calcium concentration in vascular smooth muscle cells and other cells (Non-Patent Literature 1).

In recent years, it is reported that endothelin promotes a rise in intracellular calcium concentration in epidermal melanocytes (melanin cells) to facilitate cell growth through the intracellular signal transduction system, and to enhance the activity of tyrosinase which is a rate determining enzyme in melanin synthesis (see Non-Patent Literature 2). It is also reported that endothelin is a melanocyte activating factor produced by epidermal keratinocytes (Non-Patent Literature 3) and that endothelin is an important factor in ultraviolet light-induced pigmentation or senile lentigines (Non-Patent Literatures 4 and 5).

Such biological actions of endothelin may well suggest that materials capable of suppressing endothelin action can be useful for reducing or preventing melanin production, pigmentation, or the like.

Whiteworm lichen (scientific name: *Thamnolia vermicularis* or *Thamnolia subuliformis*) is a lichen species growing in highlands of China and other areas. Whiteworm lichen is said to be effective in breaking down fat or in dieting, and also in Japan, it is often drunk in the form of tea or the like.

CITATION LIST

Non-Patent Literatures

Non-Patent Literature 1: Hirata Y. et al. (1988) Biochem. Biophys. Res. Commun. 154, 868-875
Non-Patent Literature 2: Yada et al. (1991) J. Biol. Chem. 266, 18352-18357
Non-Patent Literature 3: Imokawa et al. (1992) J. Biol. Chem. 267, 24675-24680
Non-Patent Literature 4: Imokawa et al. (1995) J. Invest. Dermatol. 105, 32-37
Non-Patent Literature 5: Kadono et al. (2001) J. Invest. Dermatol. 116, 571-577

SUMMARY OF INVENTION

Problems that the Invention is to Solve

The present invention is contemplated for providing an inhibitor of endothelin action which is capable of effectively suppressing (inhibiting) the action of endothelin. The present invention is also contemplated for providing a skin-whitening (skin-brightening) agent which is capable of suppressing the action of endothelin and suppressing melanin production.

The present invention is also contemplated for providing a method of producing a whiteworm lichen extract containing a high concentration of baeomycesic acid which is an active ingredient of the above inhibitor or skin-whitening agent.

Means to Solve the Problem

In view of the above problems, the inventors have made earnest study to find novel materials for suppressing the action of endothelin. As a result, the inventors have found that compounds represented by Formula (1) effectively suppress an endothelin-induced elevation in calcium (ion) concentration in melanocytes and that such compounds are useful as novel skin-whitening ingredients. The inventors also have made earnest study to find an extraction method capable of extracting such skin-whitening ingredients at a high concentration from whiteworm lichen. As a result, the inventors have found that when whiteworm lichen is extracted with a specific extraction solvent, a significant increase in baeomycesic acid concentration can be achieved in the resulting extract. The present invention was completed based on these findings.

The present invention provides the following means:

<1> An inhibitor of endothelin action, comprising a compound represented by Formula (1) or a salt thereof as an active ingredient.

{Chemical Formula 1}

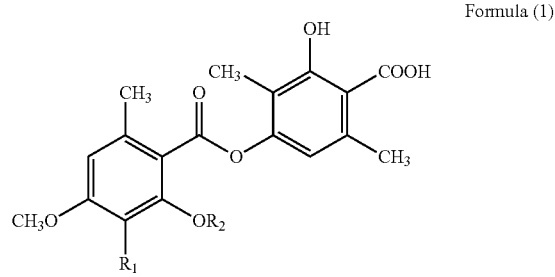

Formula (1)

wherein in Formula (1), $R_1$ represents a formyl group or an alkyl group having 1 to 4 carbon atom(s), and $R_2$ represents a hydrogen atom or an alkyl group having 1 to 4 carbon atom(s).

<2> A skin-whitening agent, comprising a compound represented by Formula (1) or a salt thereof as an active ingredient.

<3> A method of suppressing endothelin action, comprising applying a compound represented by Formula (1) or a salt thereof to skin.

<4> A method of skin whitening, comprising applying a compound represented by Formula (1) or the salt thereof to skin.

<5> Use of a compound represented by Formula (1) or a salt thereof for the preparation of a medicament having an effect of suppressing endothelin action.

<6> Use of a compound represented by Formula (1) or a salt thereof for the preparation of a medicament having an effect of skin whitening.

<7> A compound represented by Formula (1) or a salt thereof for use in suppressing endothelin action.

<8> A compound represented by Formula (1) or a salt thereof for use in skin whitening.

<9> A method of producing a whiteworm lichen extract with a high baeomycesic acid content, comprising the step of extracting whiteworm lichen with at least one solvent selected from the group consisting of an alcohol solution containing at least 60 v/v % of an alcohol, a cyclic ether, an ether having at least two oxygen atoms, and an ester having 3 to 6 carbon atoms.
<10> The method according to the item <9>, wherein an extract obtained by the extracting step has a baeomycesic acid concentration at least twice that of an extract produced with a 50 v/v % alcohol solution.
<11> The method according to the item <9> or <10>, wherein the alcohol has 1 to 4 carbon atoms.
<12> The method according to the item <9> or <10>, wherein the ether is selected from the group consisting of tetrahydrofuran, dioxane, polyethylene glycol, and polyoxyethylene methyl glucoside.
<13> The method according to the item <9> or <10>, wherein the ester is ethyl acetate.
<14> The method according to the item <9> or <10> wherein the solvent is a mixed solvent of an ester having 3 to 6 carbon atoms and an alcohol solution.
<15> An inhibitor of endothelin action, comprising a whiteworm lichen extract with a high baeomycesic acid content as an active ingredient, which the extract is obtained by the method according to any one of the items <9> to <14>.
<16> A skin-whitening agent, comprising a whiteworm lichen extract with a high baeomycesic acid content as an active ingredient, which the extract is obtained by the method according to any one of the items <9> to <14>.

Effects of the Invention

The inhibitor of endothelin action of the present invention has an excellent activity to suppress endothelin action and can effectively suppress an endothelin-induced elevation in calcium concentration in melanocytes. The skin-whitening agent of the present invention can suppress the action of endothelin on melanocytes to thereby suppress melanin production. The present invention also provides a method of producing a whiteworm lichen extract containing a high concentration of baeomycesic acid which is an active ingredient of the inhibitor and agent.

The inhibitor of endothelin action and the skin-whitening agent of the present invention are suitable for use in pharmaceuticals, quasi-pharmaceutical products, cosmetics, and other products.

Other and further features and advantages of the invention will appear more fully from the following description, taken in connection with the accompanying drawings.

MODE FOR CARRYING OUT THE INVENTION

Figure 1:
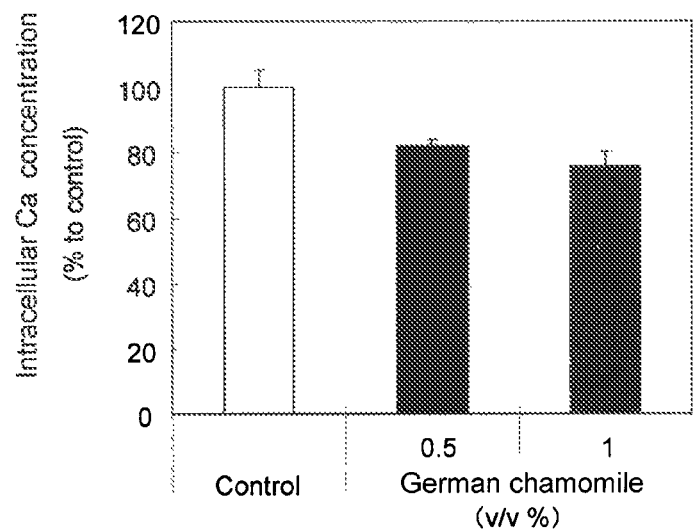
FIG. 1 is a graph showing the rate (relative value %) of rise in intracellular calcium concentration in a system where a German chamomile extract is added in a reference example for Example 1.

Hereinafter, the present invention is described in detail.
1. Compound Represented by Formula (1)

The inhibitor of endothelin action and the skin-whitening agent of the present invention contains, as an active ingredient, a compound represented by Formula (1) or a salt thereof. As demonstrated in the examples described below, the compound is highly effective in suppressing endothelin action and in suppressing melanin production.

{Chemical Formula 2}

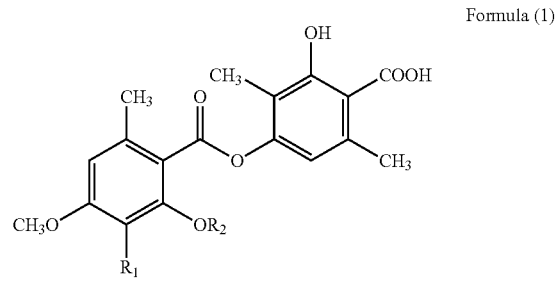

Formula (1)

In Formula (1), $R_1$ represents a formyl group or an alkyl group having 1 to 4 carbon atom(s). $R_2$ represents a hydrogen atom or an alkyl group having 1 to 4 carbon atom(s). Examples of the alkyl group having 1 to 4 carbon atom(s) include methyl, ethyl, propyl, isopropyl, n-butyl, i-butyl, sec-butyl, t-butyl.

$R_1$ is preferably a formyl group or an alkyl group having 1 to 2 carbon atom(s) (methyl, ethyl), and more preferably a formyl group or a methyl group.

$R_2$ is preferably a hydrogen atom or an alkyl group having 1 to 2 carbon atom(s) (methyl, ethyl), and more preferably a hydrogen atom or a methyl group.

The inhibitor of endothelin action and the skin-whitening agent of the present invention may include a salt of the compound represented by Formula (1) as an active ingredient. Examples of such a salt include, but are not limited to, alkali metal salts such as a lithium salt, a sodium salt, and a potassium salt; alkaline earth metal salts such as a calcium salt and a magnesium salt; alkylamine salts and quaternary ammonium salts, such as a trimethylamine salt and a triethylamine salt; alkanolamine salts such as a triethanolamine salt, a diethanolamine salt, and a monoethanolamine salt; or amino acid salts such as a lysine salt, a histidine salt, and an arginine salt. Preferred are alkali metal salts, alkanolamine salts, and amino acid salts. (Hereinafter, "a compound represented by Formula (1) or a salt thereof" is briefly and simply referred to as "the compound represented by Formula (1)".)

Specific examples of the compound represented by Formula (1) are shown below, but the present invention is not limited thereto. In the following exemplified compounds, "Me" represents a methyl group.

{Chemical Formula 3}

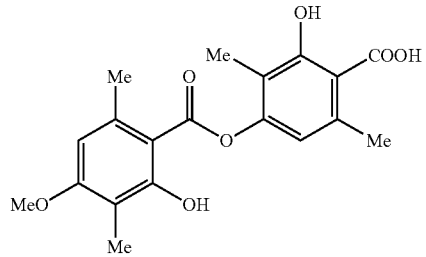

Barbatic Acid

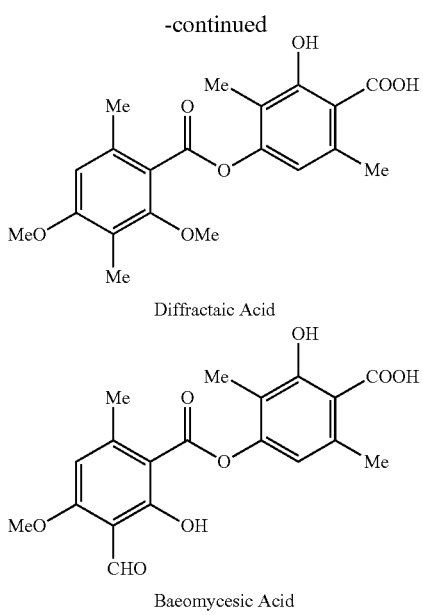

Diffractaic Acid

Baeomycesic Acid

In the inhibitor of endothelin action or the skin-whitening agent of the present invention, the compound represented by Formula (1) as an active ingredient can be used alone, or two or more kinds can be used in combination.

As demonstrated in the examples described below, the compound represented by Formula (1) can effectively suppress an endothelin-induced rise in calcium concentration in melanocytes. The compound is also effective in skin whitening because it can suppress melanin production by suppressing the action of endothelin on melanocytes.

According to the present invention, the term "skin-whitening (action)" means an action of suppressing the production of melanin pigment and thereby returning a skin color to the original transparent tone without any extra melanin, or an action of preventing and/or suppressing darkening of a skin or pigmentation such as blotches and freckles.

As the compound represented by Formula (1), a chemically synthesized compound may be used, and a compound extracted or purified from a natural product-derived material may also be used. Furthermore, a product that is commercially available as a reagent can also be used.

The compound represented by Formula (1) can be synthesized, for example, by the method described in Australian Journal of Chemistry (1975), 28(5), 1113-1124, the method described in Journal of the Pharmaceutical Society of Japan (1936), 56, 237-258, or the method described in Journal of the Pharmaceutical Society of Japan (1932), 52, 991-993.

As the reagent, a product commercially available from NAMIKI SHOJI Co., Ltd. and the like can be used.

The method of extracting and isolating the compound represented by Formula (1) from a natural product such as a plant is not particularly limited, but an example may be a method in which the plant is applied to the extraction using an appropriate solvent, and isolating the compound represented by Formula (1) from the obtained plant extract by using a technique such as chromatography.

For example, the plant to be used may be whiteworm lichen (Japanese name: Seccha or Yukicha, scientific name: *Thamnolia vermicularis*).

As a solvent that is used for the extraction, those conventionally used for the extraction of plant components can be used. Examples include water; alcohols such as methanol, ethanol, propanol and butanol; polyhydric alcohols such as ethylene glycol, propylene glycol, glycerin, and butylene glycol; ketones such as acetone and methyl ethyl ketone; esters such as methyl acetate and ethyl acetate; linear and cyclic ethers such as tetrahydrofuran and diethyl ether; polyethers such as polyethylene glycol; halogenated hydrocarbons such as dichloromethane, chloroform, and carbon tetrachloride; hydrocarbons such as hexane, cyclohexane and petroleum ether; aromatic hydrocarbons such as benzene and toluene; pyridines; supercritical carbon dioxide; oils and fats, waxes, and other oils. Alternatively, a mixture combining two or more kinds of the solvents described above can be used as the extraction solvent.

Further, with regard to the extraction condition, typical extraction conditions can be employed. For example, the above-described plant may be dipped or heated under reflux for about several minutes to several weeks at 0 to 100° C.

2. Method of Producing Baeomycesic Acid-Rich Whiteworm Lichen Extract

Baeomycesic acid, an example of the compound represented by Formula (1), is preferably produced by extracting whiteworm lichen as a raw material with at least one solvent selected from the group consisting of an aqueous alcohol solution with an alcohol content of 60% or more, a cyclic ether, an ether having two or more oxygen atoms, and an ester having 3 to 6 carbon atoms. The whiteworm lichen extract obtained by this method contains baeomycesic acid at a concentration higher than that of whiteworm lichen extracts obtained using other extraction solvents.

[Raw Material]

Whiteworm lichen for use as a raw material is a lichen belonging to the genus *Thamnolia* and the family Icmadophilaceae and known under the scientific name *Thamnolia vermicularis* (Japanese name: Seccha) or *Thamnolia subuliformis* (Japanese name: Tokiwa Mushigoke). It is known that a whiteworm lichen extract contains compounds called depsides, such as thamnolic acid, squamatic acid, and baeomycesic acid (see Japanese Journal of Food Chemistry, Vol. 14(2), 2007, pp. 63-69). It is also reported that a whiteworm lichen extract has the effect of inhibiting melanin production (see JP-A-2006-182731). It is also reported that baeomycesic acid has a vasodilating effect, a body slimming effect, and the like (see JP-A-02-223577 and US 2004-0146359 A).

In the present invention, relative lichens belonging to the above genus may also be used. These lichens are commercially available.

A mixture of *Thamnolia vermicularis* and *Thamnolia subuliformis*, may be used as a raw material, or *Thamnolia vermicularis* or *Thamnolia subuliformis* may be used alone as a raw material. *Thamnolia vermicularis* is preferably used. Any part of whiteworm lichen (such as whole, entire plant, thallus, arbuscule, frond, or fruit body) may be used, and two or more of the parts may be used in combination. Thallus or arbuscule is preferably used.

Fresh whiteworm lichen may be used as the raw material to be extracted, or to increase extraction efficiency, whiteworm lichen may be subjected to drying, shredding, grinding, or other processes.

[Extraction Solvent]

The extraction solvent can be selected from an alcohol solution containing 60% or more of an alcohol (in which examples of the alcohol include methanol, ethanol, propanol, butanol, and other alcohols; and propylene glycol, butylene glycol, and other polyhydric alcohols, and the alcohol preferably has 1 to 4 carbon atoms); a cyclic ether (e.g., tetrahydrofuran or dioxane); an ether having two or more oxygen atoms (e.g., a polyether, such as polyethylene glycol or polyoxyethylene methyl glucoside); and an ester having 3 to 6 carbon atoms (e.g., methyl acetate or ethyl acetate). In the present invention, these solvents may be used alone or in combination of two or more. In addition, the extraction may be performed using any of the solvents, which may then be replaced by any other solvent. In the producing method of the present invention, the extraction solvent used is preferably an aqueous alcohol solution with an alcohol concentration of 60% or more or ethyl acetate, more preferably an aqueous alcohol solution with an alcohol concentration of 70% or more, even more preferably an aqueous alcohol solution with an alcohol (preferably ethanol) concentration of 90% or more, still more preferably an aqueous alcohol solution with an alcohol (preferably ethanol) concentration of 95% or more. In the description, the solvent concentration is by volume (v/v) unless otherwise specified.

The extraction solvent is preferably used in an amount 1 to 200 times, more preferably 1 to 100 times, even more preferably 1 to 50 times, still more preferably 5 to 40 times, most preferably 5 to 30 times the mass of whiteworm lichen used as the raw material to be extracted.

[Extraction Method]

A method and conditions for extracting whiteworm lichen are not particularly limited, and conventional methods and conditions used for extracting lichens or plants may be used. For example, whiteworm lichen is preferably subjected to reflux under heating or immersion at 0 to 100° C. for several minutes to several weeks, in particular, preferably subjected to immersion at a temperature of around room temperature for about 1 hour to about 3 weeks. To increase the extraction efficiency, agitation may be performed together, or homogenization may be performed in the solvent.

After the extracting step, if necessary, a highly active fraction may be fractionated by any suitable separation means, such as gel filtration, chromatography, or precision distillation.

The extract obtained by the producing method of the present invention encompasses a variety of extracts obtained as described above, dilutions thereof, concentrates thereof, products obtained by purification thereof, dry powders thereof, and the like.

The whiteworm lichen extract obtained by the producing method of the present invention contains a high content of baeomycesic acid. More specifically, the whiteworm lichen extract with a high content (high concentration) of baeomycesic acid obtained according to the present invention is characterized by having a baeomycesic acid concentration twice or more higher than that of an extract obtained by extracting the same amount of whiteworm lichen with the same amount of an aqueous 50% alcohol solution under the same conditions (extraction time, extraction temperature, etc). In the present invention, the concentration of baeomycesic acid in the whiteworm lichen extract is preferably 300 ppm or more, more preferably 400 ppm or more, even more preferably 800 ppm or more based on the total mass of the extract. In the description, "ppm" is by mass unless otherwise specified.

The whiteworm lichen extract obtained by the producing method of the present invention contains baeomycesic acid at a high concentration and has a skin-whitening effect even higher than that of conventional whiteworm lichen extracts as demonstrated in the examples described below. Thus, when the whiteworm lichen extract obtained by the method is used in the inhibitor of endothelin action or the skin-whitening agent of the present invention, an even higher endothelin action-suppressing effect and an even higher skin-whitening effect can be expected.

3. Inhibitor of Endothelin Action and Skin-Whitening Agent

According to the present invention, the compound represented by Formula (1) or the whiteworm lichen extract with a high content of baeomycesic acid according to the method of the present invention may be directly used as an inhibitor of endothelin action or a skin-whitening agent. Alternatively, the compound or the extract may also be used as a formulation prepared by adding thereto an appropriate liquid or solid excipient or extending agent such as titanium oxide, calcium carbonate, distilled water, lactose or starch. In this case, the amount of the compound represented by Formula (1) in the inhibitor or the skin-whitening agent is not particularly limited, but it is preferable that the compound represented by Formula (1) be contained in an amount of 0.00001 to 5% by mass, more preferably 0.00001 to 3% by mass, and particularly preferably 0.0001 to 3% by mass. Further, the amount of the extract in the inhibitor or the skin-whitening agent is not particularly limited, but it is preferable that the extract be contained in an amount of 0.0001 to 50% by mass, more preferably 0.001 to 20% by mass, and particularly preferably 0.01 to 10% by mass.

In the skin-whitening agent of the present invention, the compound represented by Formula (1) or the whiteworm lichen extract with a high baeomycesic acid content according to the method of the present invention is incorporated as an active ingredient, and other efficacious ingredients may be incorporated. For example, other whitening agent, moisturizer, antioxidants, ultraviolet absorbents, surfactants, thickeners, coloring material, and the like can be incorporated.

In the case of preparing a composition containing such other ingredients, the amount of the compound represented by Formula (1) in the skin-whitening agent is not particularly limited, but it is preferable that the compound represented by Formula (1) be contained in an amount of 0.00001 to 5% by mass, more preferably 0.0001 to 5% by mass, and particularly preferably 0.0001 to 3% by mass. Further, the amount of the extract in the skin-whitening agent is not particularly limited, but it is preferable that the extract be contained in an amount of 0.0001 to 50% by mass, more preferably 0.001 to 20% by mass, and particularly preferably 0.01 to 10% by mass.

The inhibitor of endothelin action and the skin-whitening agent of the present invention can be used in the form of an external preparation for skin. The "external preparation for skin" means a formulation that is applied to the skin as a cosmetic material for skin, a drug for external use, a quasi-drug for external use, or the like. The dosage form can be in a wide variety of forms such as an aqueous solution system, a solubilized system, an emulsified system, a powder system, a gel system, an ointment system, a cream, water-oil biphasic system, and a water-oil-powder triphasic system. Examples of the dosage form include a face wash, a skin toner, an emulsion, a cream, a gel, an essence (serum), a facial pack, a facial mask, a foundation, an ointment, and a sheet-like product.

When used in the form of an external preparation for skin, components that are used in conventional external preparations for skin, for example, a surfactant, an oily material, a polymer compound, a preservative, efficacious ingredients other than the above, a powder, an ultraviolet absorbent, a colorant, a fragrance, an emulsification stabilizer, and a pH adjusting agent can be appropriately incorporated into the external preparation, in addition to the compound represented by Formula (1) or the whiteworm lichen extract with a high content of baeomycesic acid according to the method of the present invention. The dosage amount of the external preparation for skin containing the compound represented by Formula (1) or the whiteworm lichen extract with a high content of baeomycesic acid may vary according to the content of the active ingredient, however, for example, in the case of a cream form or an ointment form, the dosage amount is preferably 0.1 to 5 μg per 1 square centimeter of a skin, and in the case of a liquid preparation, the dosage amount of use is preferably 0.1 to 10 μg per 1 square centimeter of a skin.

EXAMPLES

Hereinafter, the present invention will be described more in detail with reference to Examples, but the present invention is not limited thereto. In the preparation examples and the examples described below, the whiteworm lichen used was *Thamnolia vermicularis*.

Preparation Example 1

Baeomycesic Acid

One L of an aqueous 95% ethanol solution was added to 41.6 g of *Thamnolia vermicularis* (available from SHINWA BUSSAN CO., LTD.), which was extracted with the solution at 30° C. for 30 days. Subsequently, the extract was subjected to filtration, and *Thamnolia vermicularis* left on the filter paper was washed with 200 mL of an aqueous 95% ethanol solution. The resulting filtrate was added to the first filtrate, so that 1,100 mL of a *Thamnolia vermicularis* extract (solid content; 2.98 g) was obtained. Subsequently, 56 mL (solid content; 151.7 mg) of the extract was fractionated by HPLC to give 28.00 mg of baeomycesic acid (18.5% yield).

The structural analysis of the isolated component was performed using NMR. The NMR spectral data of the isolated component substantially agreed with the spectral data of baeomycesic acid reported in the literature (see Japanese Journal of Food Chemistry, Vol. 14(2), 2007). Thus, the isolated component was identified as baeomycesic acid. Table 1 shows the results of the NMR structural analysis. In the table, Me represents methyl group.

TABLE 1

| | $^{13}$C-NMR (ppm) | | $^1$H-NMR (ppm) | |
|---|---|---|---|---|
| | Isolated Component | Baeomycesic Acid (literature) | Isolated Component | Baeomycesic Acid (literature) |
| 1 | 113.59 | 113.30 | | |
| 2 | 160.90 | 160.70 | | |
| 3 | 108.53 | 108.10 | | |
| 4 | 163.33 | 163.10 | | |
| 5 | 104.94 | 104.70 | 6.72 | 6.71 |
| 6 | 149.19 | 149.00 | | |
| 7 | 164.17 | 163.90 | | |
| 8 | 21.24 | 21.00 | 2.47 | 2.47 |
| 9 | 56.84 | 56.60 | 3.96 | 3.95 |
| 10 | 194.01 | 193.70 | 10.22 | 10.21 |
| 11 | 112.06 | 111.50 | | |
| 12 | 161.81 | 161.30 | | |
| 13 | 116.04 | 115.90 | | |

TABLE 1-continued

| | $^{13}$C-NMR (ppm) | | $^1$H-NMR (ppm) | |
|---|---|---|---|---|
| | Isolated Component | Baeomycesic Acid (literature) | Isolated Component | Baeomycesic Acid (literature) |
| 14 | 152.06 | 152.00 | | |
| 15 | 115.68 | 115.80 | 6.6 | 6.62 |
| 16 | 139.21 | 139.00 | | |
| 17 | 173.27 | 173.10 | | |
| 18 | 23.05 | 22.80 | 2.48 | 2.48 |
| 19 | 9.33 | 9.00 | 2.04 | 2.04 |

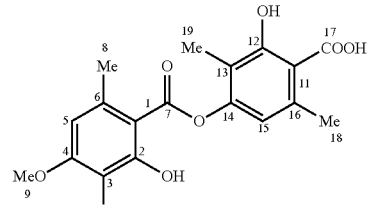

Baeomycesic Acid

Reference Example 1

Squamatic Acid

Twenty-four mL (solid content; 65.04 mg) of the *Thamnolia vermicularis* extract obtained in Preparation Example 1 was fractionated by HPLC to give 5.6 mg of squamatic acid (8.61% yield). The structural analysis of the isolated component was performed using NMR. The NMR spectral data of the isolated component substantially agreed with the spectral data of squamatic acid reported in the literature (see Yunnan Zhiwu Yanjiu, 24(4), 525-530 (2002)). Thus, the isolated component was identified as squamatic acid. Table 2 shows the results of the NMR structural analysis. In the table, Me represents methyl group.

TABLE 2

| | $^{13}$C-NMR (ppm) | | $^1$H-NMR (ppm) | |
|---|---|---|---|---|
| | Isolated Component | Squamatic Acid (literature) | Isolated Component | Squamatic Acid (literature) |
| 1 | 114.6 | 114.6 | | |
| 2 | 166.9 | 166.9 | | |
| 3 | 104.7 | 105.1 | | |
| 4 | 162.4 | 162.5 | | |
| 5 | 105.2 | 105.4 | 6.50 | 6.55 |
| 6 | 144.9 | 144.3 | | |
| 7 | 163.3 | 163 0 | | |
| 8 | 21.4 | 21.4 | 2.60 | 2.62 |
| 9 | 56.1 | 56.5 | 3.85 | 3.90 |
| 10 | 176.1 | 176.0 | | |
| 11 | 112.7 | 112.6 | | |
| 12 | 164.1 | 164.1 | | |
| 13 | 116.8 | 117.1 | | |
| 14 | 153.2 | 153.5 | | |
| 15 | 116.2 | 116.5 | 7.03 | 7.02 |
| 16 | 140.6 | 140.8 | | |
| 17 | 173.5 | 173.5 | | |

TABLE 2-continued

| | $^{13}$C-NMR (ppm) | | $^1$H-NMR (ppm) | |
|---|---|---|---|---|
| | Isolated Component | Squamatic Acid (literature) | Isolated Component | Squamatic Acid (literature) |
| 18 | 23.9 | 24.0 | 2.84 | 2.81 |
| 19 | 9.9 | 9.9 | 2.59 | 2.57 |

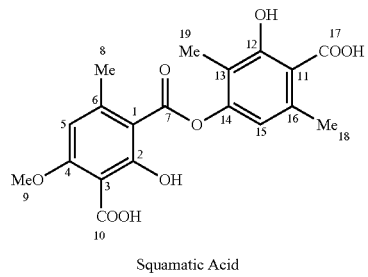

Squamatic Acid

Preparation Example 2

Barbatic Acid

Barbatic acid commercially available as a reagent (purchased from NAMIKI SHOJI Co., Ltd.) was used in the activity evaluation described below.

Preparation Example 3

Diffractaic Acid

Diffractaic acid commercially available as a reagent (purchased from NAMIKI SHOJI Co., Ltd.) was used in the activity evaluation described below.

Reference Example 2

German Chamomile Extract

Four hundred mL of an aqueous solution containing 50% of ethanol was added to 40 g of flower of German chamomile (Japanese name: Kamitsure, purchased from SHINWA BUSSAN CO., LTD.), which was extracted with the aqueous solution containing 50% of ethanol at room temperature for 14 days. After the extraction, filtration was performed, so that a German chamomile extract (221 mL) was obtained (2.63% evaporation residue).

Example 1

Examination of Endothelin Action-Suppressing Effect

Using the assay system described below, it was examined how effective each of the compounds and the extracts prepared as described above is in suppressing endothelin action.

(1) Assay System

Normal human neonatal epidermal melanocytes (NHEMs, KURABO INDUSTRIES LTD.) were seeded at $3 \times 10^4$ cells/well (200 μL/well) in 96-well plates for use in fluorometry, and cultured at 37° C. under 5% $CO_2$. The medium used was PMA (−), growth additive (HMGS)-containing Medium 254.

After culture for 3 days, the medium was removed from the culture plate by decantation, and replaced with an assay buffer containing a reagent Fluo4-AM for intracellular $Ca^{2++}$ measurement, which was followed by incubation at 37° C. for 1 hour. Subsequently, 20 seconds after the start of the measurement, the compound at a predetermined concentration was pretreated for 1 minute in a FDSS (Functional Drug Screening System) instrument, and then endothelin (ET-1, 100 nM final concentration) as a ligand was added to the wells. Fluo4-AM fluorescence was detected at the measurement wavelengths Ex. 480 nm and Em. 540 nm over time from the start of the measurement to 5 minutes later.

For each compound, the rate (%) of rise in intracellular calcium (calcium ion) concentration was calculated as a relative value (%) when an increase (Max ratio−Min ratio) in Fluo4-AM fluorescence in a control was normalized as 100. The suppressing effect of endothelin action was evaluated based on the calculated rate. In the control used, ethanol or a 10 to 95 v/v % aqueous ethanol solution was added at a final concentration of 0.1 to 0.5 v/v %.

(2) Reference Example

Evaluation of German Chamomile Extract

The German chamomile extract (2.63% evaporation residue, prepared with 50% EtOH solvent) prepared as described above was used as a positive control. It is known that German chamomile extracts can suppress an endothelin-induced rise in calcium concentration in melanocytes and can suppress melanin production.

The German chamomile extract was pretreated at final concentrations of 0.5 v/v % and 1.0 v/v % and subjected to the assay system described above. Then, the rate of rise in calcium (Ca) concentration induced by endothelin action was calculated (N=6). The results are shown in FIG. 1.

As shown in FIG. 1, it was observed that the rise in Ca concentration was suppressed in a concentration-dependent manner in the system where the German chamomile extract was added. Especially in the system at a concentration of 1 v/v %, the rise in Ca concentration was suppressed by at least 20%, and a high endothelin-suppressing effect was observed.

(3) Evaluation of the Compounds of the Present Invention

The compound prepared as described above was pretreated at the final concentration shown in Table 3 and subjected to the assay system. Then, the rate of endothelin-induced rise in Ca concentration was calculated (N=6). The results are shown in Table 3.

TABLE 3

| Compound | Concentration (μM) | Rate of rise in intracellular Ca concentration | Remarks |
|---|---|---|---|
| Baeomycesic Acid | 50 | 52.7 | This invention |
| Squamatic Acid | 50 | 95.9 | Reference example |
| Barbatic Acid | 50 | 38.4 | This invention |
| Diffractaic Acid | 50 | 28.0 | This invention |

As shown in Table 3, it was found that the endothelin-induced rise in intracellular Ca concentration was suppressed by at least 45% in every system where baeomycesic acid, barbatic acid, or diffractaic acid was added at a concentration of 50 μM. Thus, it has been demonstrated that the compound represented by Formula (1) has a high endothelin-suppressing effect and that its suppression effect is equal to or higher than that of German chamomile extracts, which are known as a skin-whitening ingredient.

On the other hand, the rise in intracellular Ca concentration was suppressed only by about 4% in the system where squamatic acid was added at a concentration of 50 μM.

Example 2

Examination of Melanin Production-Suppressing Effect

The effect of suppressing melanin production in skin was examined using the baeomycesic acid prepared as described above.

Figure 2:
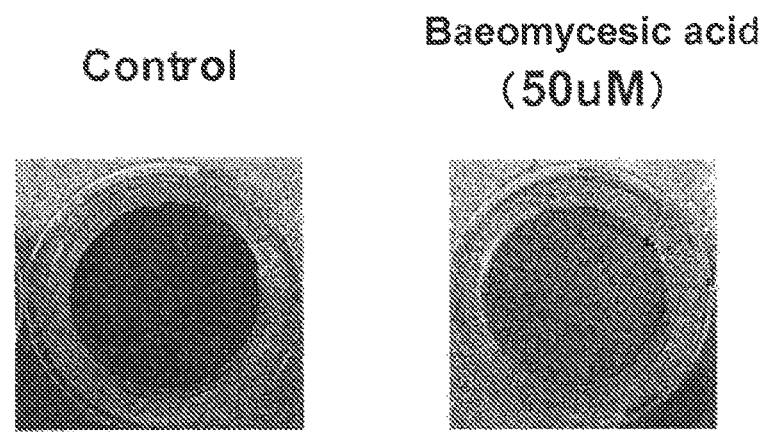
FIG. 2 is a photograph of a skin sheet cultured with addition of baeomycesic acid in Example 2.

A melanocyte-containing, 3-D cultured skin model (MEL300A, KURABO INDUSTRIES LTD.) was cultured at 37° C. under 5% $CO_2$ using an EPI-100-NMM113 medium to which endothelin-1 (ET-1) as a melanocyte activator and SCF (stem cell growth factor) were each added at a final concentration of 10 nM. From the first day of the culture, the baeomycesic acid was added at a final concentration of 50 μM (N=2). The medium was refreshed once every three days. After 14 days, the skin model was washed with PBS and photographed. The results are shown in FIG. 2. Subsequently, the cell respiration activity was measured using the Alamar Blue reagent to confirm that the final concentration was not cytotoxic (the results are not shown).

Figure 3:
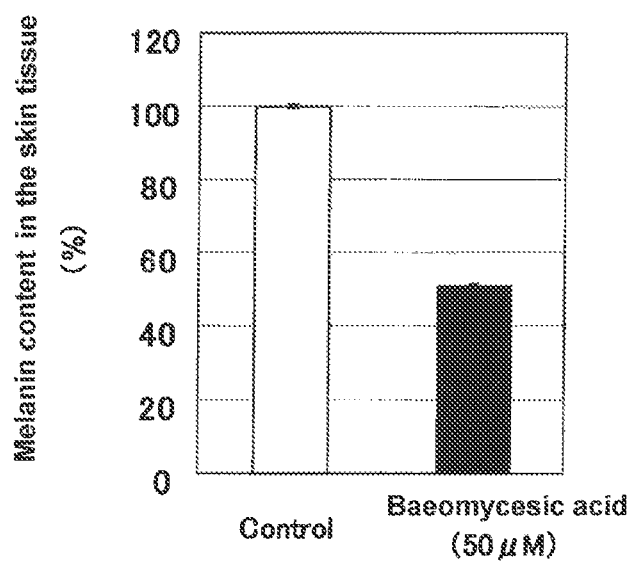
FIG. 3 is a graph showing the melanin content (relative value %) in the skin sheet cultured with addition of baeomycesic acid in Example 2.

Subsequently, the skin model cup was washed with PBS, and the skin sheet was removed with tweezers, transferred into a tube, and washed three times with PBS. The skin sheet was washed three times with 50% ethanol and twice with 100% ethanol, and then allowed to stand overnight at room temperature, so that it was completely dried. After 200 μL of 2 M NaOH was added, the skin sheet was dissolved at 100° C. A supernatant obtained by centrifugation of the solution was measured for absorbance at a wavelength of 405 nm, and then the melanin content was calculated. The results are shown in FIG. 3. The melanin content was expressed as a relative value (%) when the melanin content in a control was normalized as 100. In the control used, ethanol or a 10 to 95 v/v % aqueous ethanol solution was added at a final concentration of 0.1 to 0.5 v/v %.

As shown in FIG. 2, the system where the baeomycesic acid was added had light skin color and suppressed skin blackening caused by melanin production as compared with the control system. Also as shown in FIG. 3, the system where the baeomycesic acid was added at a nontoxic concentration showed a reduction of at least 40% in melanin content in the skin tissue, relative to the control system.

As mentioned above, it is known that endothelin acts on melanocytes to raise calcium concentration and to increase melanin production (see Yada et al. (1991) J. Biol. Chem. 266, 18352-18357, Imokawa et al. (1992) J. Biol. Chem. 267, 24675-24680). Materials capable of suppressing the action of endothelin can be useful as skin-whitening ingredients. The above examples of the present invention have actually demonstrated that materials capable of suppressing the action of endothelin on melanocytes can effectively suppress melanin production. Thus, it has been found that the compound represented by Formula (1) can effectively suppress the action of endothelin in promoting a rise in intracellular calcium concentration, and thus can suppress melanin production so that it is useful as a skin-whitening agent.

Subsequently, the effect of suppressing melanin production was exam in the same manner as described above using the squamatic acid isolated as described above. In the system where the squamatic acid was added, no significant reduction in melanin content was observed in contrast to the system where the baeomycesic acid was added.

Therefore, it has been found that baeomycesic acid contained in whiteworm lichen significantly suppresses the rise in intracellular Ca concentration induced by endothelin and significantly suppresses melanin production in skin. In contrast, squamatic acid showed almost no effect of suppressing endothelin action and almost no effect of suppressing melanin production although it is also a component contained in whiteworm lichen.

Example 3-1

To 5.0 g of *Thamnolia vermicularis* (made in China and purchased from SHINWA BUSSAN CO., LTD.) was added 100 mL of a 60% ethanol solution. The *Thamnolia vermicularis* was extracted with the ethanol solution at 40° C. for a week, which was followed by filtration, so that 75.9 g of a *Thamnolia vermicularis* extract was obtained (0.45 w/v % evaporation residue).

Example 3-2

To 5.0 g of *Thamnolia vermicularis* (made in China and purchased from SHINWA BUSSAN CO., LTD.) was added 100 mL of a 70% ethanol solution. The *Thamnolia vermicularis* was extracted with the ethanol solution at 40° C. for a week, which was followed by filtration, so that 74.6 g of a *Thamnolia vermicularis* extract was obtained (0.52 w/v % evaporation residue).

Example 3-3

To 5.0 g of *Thamnolia vermicularis* (made in China and purchased from SHINWA BUSSAN CO., LTD.) was added 100 mL of a 80% ethanol solution. The *Thamnolia vermicularis* was extracted with the ethanol solution at 40° C. for a week, which was followed by filtration, so that 72.6 g of a *Thamnolia vermicularis* extract was obtained (0.50 w/v % evaporation residue).

Example 3-4

To 5.0 g of *Thamnolia vermicularis* (made in China and purchased from SHINWA BUSSAN CO., LTD.) was added 100 mL of a 90% ethanol solution. The *Thamnolia vermicularis* was extracted with the ethanol solution at 40° C. for a week, which was followed by filtration, so that 71.7 g of a *Thamnolia vermicularis* extract was obtained (0.46 w/v % evaporation residue).

Example 3-5

To 5.0 g of *Thamnolia vermicularis* (made in China and purchased from SHINWA BUSSAN CO., LTD.) was added 100 mL of a 95% ethanol solution. The *Thamnolia vermicularis* was extracted with the ethanol solution at 40° C. for a week, which was followed by filtration, so that 69.3 g of a *Thamnolia vermicularis* extract was obtained (0.52 w/v % evaporation residue).

Example 3-6

To 5.0 g of *Thamnolia vermicularis* (made in China and purchased from SHINWA BUSSAN CO., LTD.) was added 100 mL of a 99.5% ethanol solution. The *Thamnolia vermicularis* was extracted with the ethanol solution at 40° C. for a week, which was followed by filtration, so that 67.5 g of a *Thamnolia vermicularis* extract was obtained (0.47 w/v % evaporation residue).

Reference Example 3-1

To 5.0 g of *Thamnolia vermicularis* (made in China and purchased from SHINWA BUSSAN CO., LTD.) was added 100 mL of a 10% ethanol solution. The *Thamnolia vermicularis* was extracted with the ethanol solution at 40° C. for a week, which was followed by filtration, so that 80.0 g of a *Thamnolia vermicularis* extract was obtained (0.69 w/v % evaporation residue).

Reference Example 3-2

According to the method described in JP-A-2006-182731, to 5.0 g of *Thamnolia vermicularis* (made in China and purchased from SHINWA BUSSAN CO., LTD.) was added 100 mL of a 50% ethanol solution. The *Thamnolia vermicularis* was extracted with the ethanol solution at 40° C. for a week, which was followed by filtration, so that 77.6 g of a *Thamnolia vermicularis* extract was obtained (0.51 w/v % evaporation residue).

Measurement (1) of Baeomycesic Acid Concentration

The content of baeomycesic acid in the *Thamnolia vermicularis* extract obtained in each of Examples 3-1 to 3-6 and Reference Examples 3-1 and 3-2 was analyzed using HPLC under the conditions shown below. The measurement was performed using the system and the measurement conditions shown below. The results are shown in Table 4.

Measuring system: Hitachi HPLC Multisystem Software Z30ZL200, Hitachi
HPLC Manager D-7000, Hitachi HPLC Autosampler L-7200, Hitachi HPLC
Column Oven L-7300, Hitachi HPLC Ultraviolet-Visible Detector L-7420, and Hitachi HPLC Pump L-7100

<HPLC Analysis Conditions>
Flow rate: 0.75 mL/minute
Column used: Inertsil ODS-3, 5 μm (GL Science), 3.0 I.D.×150 mm
Column temperature: 40° C.
Mobile phase: 0.1% trifluoroacetic acid-containing aqueous solution: 0.1% trifluoroacetic acid-containing methanol=30: 70 (baeomycesic acid retention time 9.06 minute)
Detection wavelength: 254 nm As shown in Table 4, the concentration of baeomycesic acid in the extract was relatively low in all cases where the extraction solvent had an alcohol concentration of 50% or less. On the other hand, it has been found that as the alcohol concentration in the extraction solvent reaches 60% or more, the concentration of baeomycesic acid in the extract sharply increases.

Example 4-1

To 2.5 g of *Thamnolia vermicularis* (purchased from SHINWA BUSSAN CO., LTD.) was added 100 mL of a 60% ethanol solution. The *Thamnolia vermicularis* was extracted with the ethanol solution at 40° C. for a week, which was followed by filtration, so that 79.8 g of a *Thamnolia vermicularis* extract was obtained (0.26 w/v % evaporation residue).

Example 4-2

To 2.5 g of *Thamnolia vermicularis* (purchased from SHINWA BUSSAN CO., LTD.) was added 100 mL of a 70% ethanol solution. The *Thamnolia vermicularis* was extracted with the ethanol solution at 40° C. for a week, which was followed by filtration, so that 78.6 g of a *Thamnolia vermicularis* extract was obtained (0.27 w/v % evaporation residue).

Example 4-3

To 2.5 g of *Thamnolia vermicularis* (purchased from SHINWA BUSSAN CO., LTD.) was added 100 mL of a 80% ethanol solution. The *Thamnolia vermicularis* was extracted with the ethanol solution at 40° C. for a week, which was followed by filtration, so that 75.8 g of a *Thamnolia vermicularis* extract was obtained (0.28 w/v % evaporation residue).

Example 4-4

To 2.5 g of *Thamnolia vermicularis* (purchased from SHINWA BUSSAN CO., LTD.) was added 100 mL of a 90% ethanol solution. The *Thamnolia vermicularis* was extracted with the ethanol solution at 40° C. for a week, which was followed by filtration, so that 74.0 g of a *Thamnolia vermicularis* extract was obtained (0.30 w/v % evaporation residue).

Example 4-5

To 2.5 g of *Thamnolia vermicularis* (purchased from SHINWA BUSSAN CO., LTD.) was added 100 mL of a 95% ethanol solution. The *Thamnolia vermicularis* was extracted with the ethanol solution at 40° C. for a week, which was followed by filtration, so that 72.6 g of a *Thamnolia vermicularis* extract was obtained (0.34 w/v % evaporation residue).

TABLE 4

| *Thamnolia vermicularis* 5.0 g | Reference Example 3-1 10% EtOH | Reference Example 3-2 50% EtOH | Example 3-1 60% EtOH | Example 3-2 70% EtOH | Example 3-3 80% EtOH | Example 3-4 90% EtOH | Example 3-5 95% EtOH | Example 3-6 99.5% EtOH |
|---|---|---|---|---|---|---|---|---|
| Yield (g) | 80.0 | 77.6 | 75.9 | 74.6 | 72.6 | 71.7 | 69.3 | 67.5 |
| Evaporation Residue (%) | 0.69 | 0.51 | 0.45 | 0.52 | 0.50 | 0.46 | 0.52 | 0.47 |
| Baeomycesic Acid concentration (ppm) | 0 | 154 | 346 | 520 | 661 | 925 | 1181 | 1167 |

Example 4-6

To 2.5 g of *Thamnolia vermicularis* (purchased from SHINWA BUSSAN CO., LTD.) was added 100 mL of a 99.5% ethanol solution. The *Thamnolia vermicularis* was extracted with the ethanol solution at 40° C. for a week, which was followed by filtration, so that 70.7 g of a *Thamnolia vermicularis* extract was obtained (0.30 w/v % evaporation residue).

Reference Example 4-1

To 2.5 g of *Thamnolia vermicularis* (purchased from SHINWA BUSSAN CO., LTD.) was added 100 mL of a 10% ethanol solution. The *Thamnolia vermicularis* was extracted with the ethanol solution at 40° C. for a week, which was followed by filtration, so that 86.2 g of a *Thamnolia vermicularis* extract was obtained (0.36 w/v % evaporation residue).

Reference Example 4-2

To 2.5 g of *Thamnolia vermicularis* (purchased from SHINWA BUSSAN CO., LTD.) was added 100 mL of a 50% ethanol solution. The *Thamnolia vermicularis* was extracted with the ethanol solution at 40° C. for a week, which was followed by filtration, so that 81.7 g of a *Thamnolia vermicularis* extract was obtained (0.29 w/v % evaporation residue).

Measurement (2) of Baeomycesic Acid Concentration

The concentration of baeomycesic acid in the extract obtained in each of Examples 4-1 to 4-6 and Reference Examples 4-1 and 4-2 was measured in the same manner as in the measurement (1) of baeomycesic acid concentration. The results are shown in Table 5.

TABLE 5

| *Thamnolia vermicularis* 2.5 g | Reference Example 4-1 10% EtOH | Reference Example 4-2 50% EtOH | Example 4-1 60% EtOH | Example 4-2 70% EtOH | Example 4-3 80% EtOH | Example 4-4 90% EtOH | Example 4-5 95% EtOH | Example 4-6 99.5% EtOH |
|---|---|---|---|---|---|---|---|---|
| Yield (g) | 86.2 | 81.7 | 79.8 | 78.6 | 75.8 | 74.0 | 72.6 | 70.7 |
| Evaporation Residue (%) | 0.36 | 0.29 | 0.26 | 0.27 | 0.28 | 0.30 | 0.34 | 0.30 |
| Baeomycesic Acid concentration (ppm) | 0 | 113 | 284 | 420 | 642 | 893 | 1085 | 1063 |

As shown in Table 5, the concentration of baeomycesic acid in the extract was relatively low in all cases where the extraction solvent had an alcohol concentration of 50% or less. On the other hand, it has been found that as the alcohol concentration in the extraction solvent reaches 60% or more, the concentration of baeomycesic acid in the extract sharply increases. Further, a comparison with the results in Table 4 shows that the smaller the amount of *Thamnolia vermicularis* used relative to the amount of the solvent, the more significant the rise in baeomycesic acid concentration, which is associated with the change in alcohol concentration.

Example 5-1

To 5.0 g of *Thamnolia vermicularis* (purchased from SHINWA BUSSAN CO., LTD.) was added 103 mL of a 100% 1,3-butanediol. The *Thamnolia vermicularis* was extracted with the ethanol solution at 40° C. for a week, which was followed by filtration, so that 86.95 g of a *Thamnolia vermicularis* extract was obtained (0.26 w/v % evaporation residue).

Reference Example 5-1

To 5.0 g of *Thamnolia vermicularis* (purchased from SHINWA BUSSAN CO., LTD.) was added 100 mL of a 50% 1,3-butanediol. The *Thamnolia vermicularis* was extracted with the ethanol solution at 40° C. for a week, which was followed by filtration, so that 86.07 g of a *Thamnolia vermicularis* extract was obtained (0.35 w/v % evaporation residue).

Measurement (3) of Baeomycesic Acid Concentration

The concentration of baeomycesic acid in the extract obtained in each of Example 5-1 and Reference Example 5-1 was measured in the same manner as in the measurement (1) of baeomycesic acid concentration. The results are shown in Table 6.

TABLE 6

|  | Reference Example 5-1 50% BG | Example 5-1 100% BG |
|---|---|---|
| Yield (g) | 86.07 | 86.95 |
| Evaporation Residue (%) | 0.35 | 0.26 |
| Baeomycesic Acid concentration (ppm) | 86 | 594 |

BG = 1,3-butylene glycol

As shown in Table 6, the extract produced using 50% 1,3-butylene glycol as a solvent had a low baeomycesic acid concentration, whereas the extract produced using 100% 1,3-butylene glycol had a very high baeomycesic acid concentration.

Example 6-1

To 2.5 g of *Thamnolia vermicularis* (purchased from SHINWA BUSSAN CO., LTD.) was added 100 mL of tetrahydrofuran (THF). The *Thamnolia vermicularis* was extracted with the ethanol solution at 40° C. for a week, which was followed by filtration, so that 75.3 g of a *Thamnolia vermicularis* extract was obtained (0.32 w/v % evaporation residue).

Example 6-2

To 2.5 g of *Thamnolia vermicularis* (purchased from SHINWA BUSSAN CO., LTD.) was added 100 mL of 1,4-dioxane. The *Thamnolia vermicularis* was extracted with the ethanol solution at 40° C. for a week, which was followed by filtration, so that 93.4 g of a *Thamnolia vermicularis* extract was obtained (0.32 w/v % evaporation residue).

Example 6-3

To 2.5 g of *Thamnolia vermicularis* (purchased from SHINWA BUSSAN CO., LTD.) was added 100 mL of polyethylene glycol (PEG200). The *Thamnolia vermicularis* was extracted with the ethanol solution at 40° C. for a week, which was followed by filtration, so that 100.1 g of a *Thamnolia vermicularis* extract was obtained.

Example 6-4

To 2.5 g of *Thamnolia vermicularis* (purchased from SHINWA BUSSAN CO., LTD.) was added 100 mL of polyethylene glycol (PEG400). The *Thamnolia vermicularis* was extracted with the ethanol solution at 40° C. for a week, which was followed by filtration, so that 100.0 g of a *Thamnolia vermicularis* extract was obtained.

Example 6-5

To 2.5 g of *Thamnolia vermicularis* (purchased from SHINWA BUSSAN CO., LTD.) was added 100 mL of

Reference Example 6-1

To 2.5 g of *Thamnolia vermicularis* (purchased from SHINWA BUSSAN CO., LTD.) was added 100 mL of diethyl ether. The *Thamnolia vermicularis* was extracted with the ethanol solution at 40° C. for a week, which was followed by filtration, so that 60.7 g of a *Thamnolia vermicularis* extract was obtained (0.03 w/v % evaporation residue).

Reference Example 6-2

To 2.5 g of *Thamnolia vermicularis* (purchased from SHINWA BUSSAN CO., LTD.) was added 100 mL of palmityl-1,3-dimethyl butyl ether. The *Thamnolia vermicularis* was extracted with the ethanol solution at 40° C. for a week, which was followed by filtration, so that 70.5 g of a *Thamnolia vermicularis* extract was obtained.

Measurement (4) of Baeomycesic Acid Concentration

The concentration of baeomycesic acid in the extract obtained in each of Examples 6-1 to 6-7 and Reference Examples 6-1 and 6-2 was measured in the same manner as in the measurement (1) of baeomycesic acid concentration. The results are shown in Table 7.

TABLE 7

|  | Reference Example 6-1 Diethyl ether | Reference Example 6-2 Palmityl-1,3-dimethyl buthyl ether | Example 6-1 THF | Example 6-2 1,4-dioxane | Example 6-3 PEG200 | Example 6-4 PEG400 | Example 6-5 PEG600 | Example 6-6 Glucam E-10 | Example 6-7 Glucam E-20 |
|---|---|---|---|---|---|---|---|---|---|
| Yield (g) | 60.7 | 70.5 | 75.3 | 93.4 | 100.1 | 100.0 | 98.1 | 74.4 | 111.3 |
| Evaporation Residue (%) | 0.03 | — | 0.32 | 0.32 | — | — | — | — | — |
| Baeomycesic Acid concentration (ppm) | 265 | 5 | 1690 | 1625 | 1590 | 1396 | 1497 | 859 | 759 | polyethylene glycol (PEG600). The *Thamnolia vermicularis* was extracted with the ethanol solution at 40° C. for a week, which was followed by filtration, so that 98.1 g of a *Thamnolia vermicularis* extract was obtained.

Example 6-6

To 2.5 g of *Thamnolia vermicularis* (purchased from SHINWA BUSSAN CO., LTD.) was added 100 mL of polyoxyethylene methyl glucoside (trade name: Glucam E-10, manufactured by Noveon, Inc.) The *Thamnolia vermicularis* was extracted with the polyoxyethylene methyl glucoside at 40° C. for a week, which was followed by decantation to separate the extract from the *Thamnolia vermicularis* residue, so that 74.4 g of a *Thamnolia vermicularis* extract was obtained.

Example 6-7

To 2.5 g of *Thamnolia vermicularis* (purchased from SHINWA BUSSAN CO., LTD.) was added 100 mL of polyoxyethylene methyl glucoside (trade name: Glucam E-20, manufactured by Noveon, Inc.) The *Thamnolia vermicularis* was extracted with the polyoxyethylene methyl glucoside at 40° C. for a week, which was followed by decantation to separate the extract from the *Thamnolia vermicularis* residue, so that 111.3 g of a *Thamnolia vermicularis* extract was obtained.

The results in Table 7 show that the extracts (Reference Examples 6-1 and 6-2) produced using a chain ether having one oxygen atom as a solvent had a low baeomycesic acid concentration, whereas the extracts (Examples 6-1 to 6-7) produced using a cyclic ether or an ether having two or more oxygen atoms had a very high baeomycesic acid concentration.

Example 7-1

To 2.5 g of *Thamnolia vermicularis* (purchased from SHINWA BUSSAN CO., LTD.) was added 100 mL of ethyl acetate. The *Thamnolia vermicularis* was extracted with the ethanol solution at 40° C. for a week, which was followed by filtration, so that 81.3 g of a *Thamnolia vermicularis* extract was obtained (0.14 w/v % evaporation residue).

Example 7-2

To 2.5 g of *Thamnolia vermicularis* (purchased from SHINWA BUSSAN CO., LTD.) was added a mixed solvent of 50 mL of ethyl acetate and 50 mL of 99.5% ethanol. The *Thamnolia vermicularis* was extracted with the mixed solvent at 40° C. for a week, which was followed by filtration, so that 76.2 g of a *Thamnolia vermicularis* extract was obtained (0.34 w/v % evaporation residue).

Example 7-3

To 2.5 g of *Thamnolia vermicularis* (purchased from SHINWA BUSSAN CO., LTD.) was added a mixed solvent of 50 mL of ethyl acetate and 50 mL of 95% ethanol. The *Thamnolia vermicularis* was extracted with the mixed solvent at 40° C. for a week, which was followed by filtration, so that 77.2 g of a *Thamnolia vermicularis* extract was obtained (0.37 w/v % evaporation residue).

Example 7-4

To 2.5 g of *Thamnolia vermicularis* (purchased from SHINWA BUSSAN CO., LTD.) was added a mixed solvent of 50 mL of ethyl acetate and 50 mL of 50% ethanol. The *Thamnolia vermicularis* was extracted with the mixed solvent at 40° C. for a week, which was followed by filtration, so that 80.1 g of a *Thamnolia vermicularis* extract was obtained (0.44 w/v % evaporation residue).

Reference Example 7-1

To 2.5 g of *Thamnolia vermicularis* (purchased from SHINWA BUSSAN CO., LTD.) was added 100 mL of chloroform. The *Thamnolia vermicularis* was extracted with the ethanol solution at 40° C. for a week, which was followed by filtration, so that 132.6 g of a *Thamnolia vermicularis* extract was obtained (0.04 w/v % evaporation residue).

Reference Example 7-2

To 5.0 g of *Thamnolia vermicularis* (purchased from SHINWA BUSSAN CO., LTD.) was added 100 mL of hexane. The *Thamnolia vermicularis* was extracted with the ethanol solution at 40° C. for a week, which was followed by filtration, so that 51.8 g of a *Thamnolia vermicularis* extract was obtained (0.02 w/v % evaporation residue).

Reference Example 7-3

To 2.5 g of *Thamnolia vermicularis* (purchased from SHINWA BUSSAN CO., LTD.) was added 100 mL of toluene. The *Thamnolia vermicularis* was extracted with the ethanol solution at 40° C. for a week, which was followed by filtration, so that 70.9 g of a *Thamnolia vermicularis* extract was obtained (0.01 w/v % evaporation residue).

Measurement (5) of Baeomycesic Acid Concentration

The concentration of baeomycesic acid in the extract obtained in each of Examples 7-1 to 7-4 and Reference Examples 7-1 to 7-3 was measured in the same manner as in the measurement (1) of baeomycesic acid concentration. The results are shown in Table 8.

As shown in Table 8, the extracts produced using a hydrocarbon solvent or a halide solvent had a low baeomycesic acid concentration, whereas the extracts produced using ethyl acetate or a mixed solvent thereof had a very high baeomycesic acid concentration.

Example 8

Examination of Endothelin Action-Suppressing Effect

1. *Thamnolia vermicularis* Extract

Using the assay system of Example 1, it was examined how effective the *Thamnolia vermicularis* extracts obtained in Example 3 are in suppressing endothelin action.

The samples used in the evaluation were the extracts obtained in Examples 3-1, 3-2, 3-3, 3-5, and 3-6 or dilutions thereof, and the extracts obtained in Reference Examples 3-1 and 3-2. These extracts were each pretreated at the evaluation concentration shown in Table 9 below, and then subjected to the assay system described above. The rate of endothelin-induced rise in Ca concentration was calculated (N=6). In the examination, the solvent in each extract was replaced with DMSO, and then the resulting extract was added at 0.6 v/v % and evaluated. In the control sample, DMSO was added at 0.6 v/v %. The results are shown in Table 9.

2. German Chamomile Extract

The German chamomile extract obtained in Reference Example 2 was pretreated at a final concentration of 0.5 v/v % and then subjected to the same assay system as in the case of the *Thamnolia vermicularis* extract. The rate of endothelin-induced rise in Ca concentration was calculated (N=6). The results are shown in Table 9.

TABLE 9

| Sample | | Baeomycesic acid concentration (ppm) | Rate of rise in intracellular Ca concentration (%) | Remarks |
|---|---|---|---|---|
| 1 | 10% EtOH Extract | 0 | 100 | Reference Example 3-1 |
| 2 | 50% EtOH Extract | 154 | 95 | Reference Example 3-2 |
| 3 | 60% EtOH Extract | 346 | 85 | Example 3-1 |
| 4 | 70% EtOH Extract (dilution) | 425 | 84 | Example 3-2 (dilution) |
| 5 | 70% EtOH Extract | 520 | 78 | Example 3-2 |
| 6 | 80% EtOH Extract (dilution) | 625 | 76 | Example 3-3 (dilution) |
| 7 | 95% EtOH Extract | 1181 | 63 | Example 3-5 |

TABLE 8

| | Reference Example 7-1 Chloroform | Reference Example 7-2 Hexane | Reference Example 7-3 Toluene | Example 7-1 Ethyl acetate | Example 7-2 Ethyl acetate 99.5% EtOH | Example 7-3 Ethyl acetate 95% EtOH | Example 7-4 Ethyl acetate 50% EtOH |
|---|---|---|---|---|---|---|---|
| Yield (g) | 132.6 | 51.8 | 70.9 | 81.3 | 76.2 | 77.2 | 80.1 |
| Evaporation Residue (%) | 0.04 | 0.02 | 0.01 | 0.14 | 0.34 | 0.37 | 0.44 |
| Baeomycesic Acid concentration (ppm) | 214 | 0 (Below detection limit) | 21 | 1148 | 1509 | 1619 | 1748 |

TABLE 9-continued

| Sample | | Baeomycesic acid concentration (ppm) | Rate of rise in intracellular Ca concentration (%) | Remarks |
|---|---|---|---|---|
| 8 | 99.5% EtOH Extract | 1167 | 58 | Example 3-6 |
| 9 | German chamomile extract | — | 82 | Reference Example 2 |

As shown in Table 9, almost no change in the rate of rise in intracellular Ca concentration was observed in the system where the extract produced using a solvent with an alcohol concentration of at most 50% was added (samples 1 and 2). In contrast, the rate of endothelin-induced rise in intracellular Ca concentration was significantly reduced in the system where the extract produced using a solvent with an alcohol concentration of at least 60% was added (samples 3 to 8). The effect of each of samples 3 to 8 in suppressing the rise in intracellular Ca concentration was equal to or higher than that of the German chamomile extract (sample 9), which is known as a skin-whitening ingredient.

The above results have demonstrated that the whiteworm lichen extract of the present invention obtained with the specified extraction solvent has an excellent effect of suppressing endothelin action.

Prescription Example

A lotion, an emulsion, a serum and a cream having the compositions shown below are respectively prepared by conventional methods, using the compound obtained in the Preparation Examples 1 to 3 as an active ingredient.

1. Preparation of Lotion

| (Component) | (Content: mass %) |
|---|---|
| 1,3-Butylene glycol | 8.0 |
| Glycerol | 5.0 |
| Ethanol | 3.0 |
| Baeomycesic acid | 0.0001 |
| Chamomile extract | 3.0 |
| Bellflower extract | 1.0 |
| Clove extract | 1.0 |
| Xanthane gum | 0.1 |
| Hyaluronic acid | 0.1 |
| Disodium hydrogen phosphate | 0.1 |
| Sodium dihydrogen phosphate | 0.1 |
| Glucoside 2-ascorbate | 2.0 |
| Purified water | Balance |
| Perfume | Moderate amounts |
| Preservative | Moderate amounts |

2. Preparation of Emulsion

| (Component) | (Content: mass %) |
|---|---|
| Barbatic acid | 0.001 |
| Chamomile extract | 1.0 |
| Bellflower extract | 1.0 |
| Althea extract | 2.0 |
| Squalane | 3.0 |
| Oil of olive | 3.0 |
| Glycerol | 5.0 |
| Polyoxyethylene hydrogenated castor oil (Number of added moles of ethylene oxide: 40) | 1.0 |
| Carboxyvinyl polymer | 0.2 |
| Potassium hydroxide | 0.1 |
| Xanthane gum | 0.2 |
| Disodium edetate | 0.02 |
| Purified water | Balance |
| Preservative | Moderate amounts |

3. Preparation of Serum

| (Component) | (Content: mass %) |
|---|---|
| Diffractaic acid | 0.001 |
| Chamomile extract | 1.0 |
| Bellflower extract | 1.0 |
| Clove extract | 1.0 |
| Carboxyvinyl polymer | 0.2 |
| Acrylate•methacrylate alkyl copolymer | 0.2 |
| Potassium hydroxide | 0.2 |
| Xanthane gum | 0.1 |
| Hyaluronic acid | 0.2 |
| Sodium citrate | 0.15 |
| Citric acid | 0.03 |
| Glycerol | 10.0 |
| 1,3-Butylene glycol | 5.0 |
| Disodium edetate | 0.05 |
| Purified water | Balance |
| Preservative | Moderate amounts |
| Perfume | Moderate amounts |

4. Preparation of Serum

| (Component) | (Content: mass %) |
|---|---|
| Baeomycesic acid | 0.001 |
| Chamomile extract | 1.0 |
| Clove extract | 1.0 |
| Bellflower extract | 1.0 |
| Xanthane gum | 0.2 |
| Carboxymethylcellulose | 0.2 |
| Carboxyvinyl polymer | 0.2 |
| Potassium hydroxide | 0.1 |
| Citric acid | 0.03 |
| Sodium citrate | 0.15 |
| Glycerol | 5.0 |
| Propylene glycol | 3.0 |
| Polyethylene glycol (number average molecular weight 1500) | 1.0 |
| Polyethylene glycol monostearate | 0.5 |
| Purified water | Balance |
| Preservative | Moderate amounts |

5. Preparation of Cream

| (Component) | (Content: mass %) |
|---|---|
| Diffractaic acid | 0.001 |
| Chamomile extract | 2.0 |
| Bellflower extract | 2.0 |
| Clove extract | 2.0 |
| Methylpolysiloxane | 3.0 |
| Squalane | 2.0 |
| Neopentyl glycol dicaprate | 3.0 |
| Stearyl alcohol | 1.5 |
| Cetanol | 1.0 |
| Polyoxyethylene hydrogenated castor oil (Number of added moles of ethylene oxide: 60) | 0.5 |
| Acrylate•methacrylate alkyl copolymer | 0.3 |
| Potassium hydroxide | 0.15 |
| Xanthane gum | 0.1 |
| Disodium edetate | 0.05 |
| Purified water | Balance |
| Preservative | Moderate amounts |
| Perfume | Moderate amounts |

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2010-277001 filed in Japan on Dec. 13, 2010, and Patent Application No. 2010-277002 filed in Japan on Dec. 13, 2010, each of which is entirely herein incorporated by reference.

What is claimed is:

1. A method of skin whitening, comprising applying, to skin, a preparation that contains a compound having the structure of Formula (1) or a salt thereof:

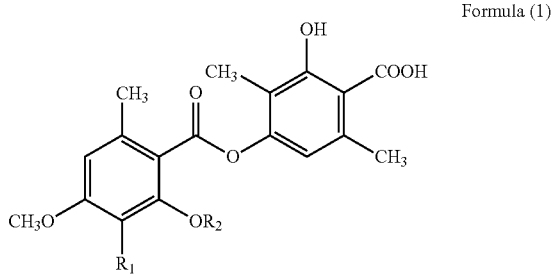

Formula (1)

wherein in Formula (1), $R_1$ is a formyl group or an alkyl group having 1 to 4 carbon atom(s), and $R_2$ is an alkyl group having 1 to 4 carbon atom(s);

wherein the compound having the structure of Formula (1) or salt thereof suppresses endothelin-induced elevation in calcium concentration in melanocytes in the skin; and whitening the skin as a result of the suppressing.

2. The method of claim 1, wherein the compound having the structure of Formula (1) or salt thereof is diffractaic acid.

3. The method of claim 1, wherein the preparation contains 0.00001 to 5% by mass of the compound having the structure of Formula (1) or salt thereof.

4. The method of claim 3, wherein the preparation is a cream or ointment.

5. The method of claim 4, wherein the compound having the structure of Formula (1) or salt thereof is applied in a dose of 0.1 to 5 μg per square centimeter of skin.

6. The method of claim 3, wherein the preparation is a liquid preparation.

7. The method of claim 6, wherein the compound is applied in a dose of 0.1 to 10 μg per square centimeter of skin.

8. The method of claim 3, wherein the compound is diffractaic acid.

9. The method of claim 1, wherein the preparation comprises a mixture of at least two compounds of Formula (1) one of which is diffractaic acid.

* * * * *